(12) United States Patent
Yamaguchi et al.

(10) Patent No.: US 8,268,951 B2
(45) Date of Patent: Sep. 18, 2012

(54) COMPOSITION COMPRISING A FLUORINE-CONTAINING ORGANOPOLYSILOXANE AND A PROCESS FOR PREPARING THE SAME

(75) Inventors: Hiromasa Yamaguchi, Annaka (JP);
Teruki Ikeda, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 13/040,448

(22) Filed: Mar. 4, 2011

(65) Prior Publication Data
US 2011/0218284 A1   Sep. 8, 2011

(30) Foreign Application Priority Data

Mar. 5, 2010   (JP) .................................. 2010-49640

(51) Int. Cl.
*C08G 77/24* (2006.01)
*C08G 77/22* (2006.01)
*C08G 77/04* (2006.01)

(52) U.S. Cl. ................. 528/30; 528/10; 528/12; 528/31; 528/32; 528/33

(58) Field of Classification Search .............. 528/10, 528/12, 30, 31, 32, 33
See application file for complete search history.

(56) References Cited

U.S. PATENT DOCUMENTS

| | | | |
|---|---|---|---|
| 4,029,629 A * | 6/1977 | Jeram | 523/203 |
| 4,340,709 A * | 7/1982 | Jeram et al. | 528/15 |
| 4,348,531 A * | 9/1982 | Evans | 556/453 |
| 4,529,752 A * | 7/1985 | Bluestein | 523/214 |
| 4,585,848 A * | 4/1986 | Evans et al. | 528/15 |
| 5,216,104 A * | 6/1993 | Okami et al. | 528/15 |
| 5,302,632 A | 4/1994 | Maxson | |
| 6,251,975 B1 * | 6/2001 | Kobayashi et al. | 524/263 |
| 6,747,115 B2 | 6/2004 | Sakuta | |
| 8,058,381 B2 * | 11/2011 | Ikeno | 528/36 |
| 2002/0058053 A1 | 5/2002 | Nakanishi et al. | |
| 2003/0092907 A1 * | 5/2003 | Snow et al. | 540/128 |
| 2005/0008597 A1 * | 1/2005 | Furukawa et al. | 424/70.12 |
| 2008/0311060 A1 | 12/2008 | Sakuta et al. | |
| 2011/0104470 A1 * | 5/2011 | Anderson et al. | 428/221 |

FOREIGN PATENT DOCUMENTS

| | | |
|---|---|---|
| JP | 2001-055307 | 2/2001 |
| JP | 2005-314372 | 11/2005 |
| JP | 2008-115358 A | 5/2008 |
| JP | 4341871 B2 | 10/2009 |

OTHER PUBLICATIONS

Extended European Search Report dated Jul. 21, 2011 for Application No. 11156885.3.
Japanese Office Action dated Apr. 26, 2012. 2010-049640.

* cited by examiner

*Primary Examiner* — Robert S Loewe
(74) *Attorney, Agent, or Firm* — Birch, Stewart, Kolasch & Birch, LLP

(57) ABSTRACT

Present invention provides a fluorine-containing organopolysiloxane composition comprising a fluorine-containing silicone polymer having a three-dimensional, cross-linked structure, prepared by addition polymerizing the following (A), (B) and (C) and containing 10 to 30 mass % of the fluorine atoms, relative to a total mass of (A) to (C), (A) a vinyl group-containing organopolysiloxane represented by the following formula (1):

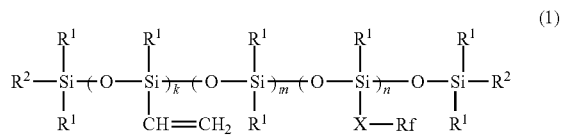

(B) an organohydrogenpolysiloxane represented by the following formula (2):

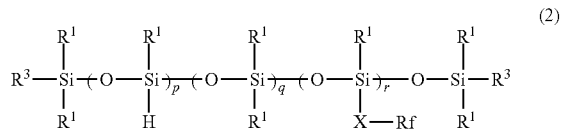

and
(C) an organopolysiloxane having a reactive group on one end alone and represented by the following formula (3),

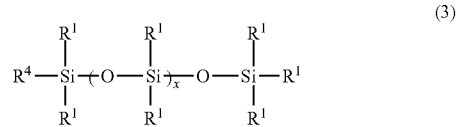

and further comprising
(D) a low viscosity silicone oil with a dynamic viscosity of 50 mm²/s or less at 25 degrees C.

7 Claims, No Drawings

COMPOSITION COMPRISING A FLUORINE-CONTAINING ORGANOPOLYSILOXANE AND A PROCESS FOR PREPARING THE SAME

CROSS-REFERENCE

This application claims the benefits of Japanese Patent Application No. 2010-049640, filed on Mar. 5, 2010, the contents of which are incorporated herein by reference.

FIELD OF THE INVENTION

The present invention relates to a fluorine-containing organopolysiloxane composition which has good water- and oil-repellency, swellability with low viscosity silicone oils, and good affinity with other materials and to a process for preparing the same.

BACKGROUND OF THE INVENTION

Fluorine-modified silicone compounds have very small surface energy and, accordingly, have unique properties such as water- and oil-repellency, chemical resistance, lubricating property, releasing property, and anti-fouling property. Therefore, they find applications, on account of such properties, as water- and oil-repelling agents, water- and oil-repellent and anti-fouling agents, additives in wax, oil proof agents, mold release agents, lubricating agents, in cosmetics, and in protecting films. However, the low surface energy of the fluorine-modified silicone compounds leads to very poor compatibility and affinity with other materials such as organic solvents or oil agents, paints, cosmetics and various coating materials. Therefore, it has been pointed out that where a fluorine-modified silicone compound is added to various industrial materials to provide the afore-mentioned properties, problems arise, for instance, in dispersion stability and, therefore, the application of the fluorine-modified silicone compounds is difficult. Accordingly, there is a need for developing fluorine-modified silicone compounds which are excellent in affinity with other materials, but without the aforesaid problem.

Low viscosity silicone oils spread easily and are safe and, therefore, recently gather attention and is considered to be used in a variety of fields. When preparing a pasty composition having no flowability, based on a low viscosity silicone oil, a large amount of a thickening agent is necessary. As a result, it is difficult to obtain a smooth and homogeneous composition and, further, the stability is bad. The following Patent Literature 1 describes that a silicone polymer having side chains in a part of a cross-linked structure thereof provides a composition which is homogeneous, pasty and swellable with organic oils. Although the silicone composition forms a water-repellent film after applied, the film shows very poor oil-repellency and unsatisfactory abrasion resistance.

The following Patent Literature 2 describes a composition which is homogeneous, pasty, good in water- and oil-repellency, and swellable with fluorine-modified silicone oils which have a high content of fluorine-substituted alkyl groups, such as penta-3,3,3-trifluoropropylpentamethyl cyclopentasiloxane, and. However, the composition is bad in affinity with silicone materials which do not contain a fluorine-substituted alkyl group or with other materials. The composition is not stable over time, either.

Prior Literatures

Patent Literatures

[Patent Literature 1] Japanese Patent Application Laid-Open No. 2008-115358
[Patent Literature 2] Japanese Patent No. 4341871

SUMMARY OF THE INVENTION

Problems to be Solved by the Invention

The present inventors previously found that a pasty composition comprising a cross-linked perfluoropolyether polymer as a thickener in a low viscosity fluorine-modified oil has a good water- and oil-repellency, a non-oily touch characteristic to perfluoropolyether oil and is stable (Japanese Patent Application Laid-Open No. 2010-189602). However, that pasty composition does not have enough affinity with other materials such as paints, cosmetics and various coating materials.

The purpose of the present invention is to provide a fluorine-containing silicone composition which is good in water- and oil-repellency and good affinity with other materials such as organic solvents, oil agents, paints, cosmetics and various coating materials and, in particular, which is swellable with low viscosity silicone oils, and to provide a homogeneous pasty composition comprising this fluorine-containing silicone composition.

Means to Solve the Problems

The present inventors has found that a fluorine-containing silicone polymer with a three-dimensional, cross-linked structure comprising a particular amount, per molecule, of fluorine atoms and a particular amount, per molecule, of silicone side chains is very swellable with low viscosity silicone oils to provide a homogeneous pasty composition.

The present invention provides a fluorine-containing organopolysiloxane composition comprising
a fluorine-containing silicone polymer having a three-dimensional, cross-linked structure, prepared by addition polymerizing the following (A), (B) and (C) and containing 10 to 30 mass % of the fluorine atoms, relative to a total mass of (A) to (C),
(A) a vinyl group-containing organopolysiloxane represented by the following formula (1):

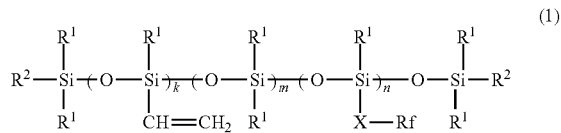

wherein Rf is a perfluoroalkyl group having 1 to 10 carbon atoms or a perfluoropolyether group having 3 to 30 carbon atoms; $R^1$ is, independently of each other, a monovalent hydrocarbon group having 1 to 10 carbon atoms without any aliphatic unsaturated bond; $R^2$ is, independently of each other, a vinyl group or a monovalent hydrocarbon group having 1 to 10 carbon atoms without any aliphatic unsaturated bond; k is an integer of 0 to 10, provided that the organopolysiloxane has at least two, per molecule, vinyl groups bonded to silicon atoms; X is a divalent organic group, m is an integer of 0 to 200, and n is an integer of 0 to 100, (B) an organohydrogenpolysiloxane represented by the following formula (2):

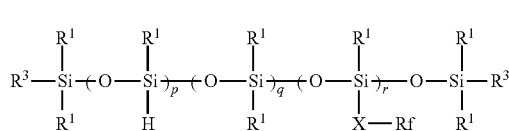

wherein $R^3$ is, independently of each other, a hydrogen atom or a monovalent hydrocarbon group having 1 to 10 carbon atoms without any aliphatic unsaturated bond; p is an integer of 0 to 10, provided that the organopolysiloxane has at least two, per molecule, hydrogen atoms bonded to silicon atoms; q is an integer of 0 to 200; r is an integer of 0 to 100, provided that n in formula (1) and r in formula (2) are not simultaneously zero; and at least either one of the number of the vinyl groups bonded to silicon atoms in formula (1) or the number of the hydrogen atoms bonded to silicon atoms in formula (2) is at least three; and Rf, X, and $R^1$ are as defined above, and (C) an organopolysiloxane having a reactive group on one end alone and represented by the following formula (3),

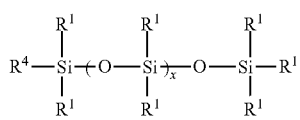

wherein $R^4$ is a hydrogen atom or a vinyl group, x is an integer of 0 to 100, and $R^1$ is as defined above, and further comprising (D) a low viscosity silicone oil with a dynamic viscosity of 50 mm²/s or less at 25 degrees C., and a process for preparing the composition.

Effects of the Invention

The fluorine-containing silicone polymer of the present invention has the particular amount of silicone side chain and, therefore, is swellable with low viscosity silicone oils to provide a homogeneous and stable pasty silicone composition. The fluorine-containing silicone polymer of the present invention has the particular amount of fluorine atoms and, therefore, is good in water- and oil-repellency and provides very light and smooth touch.

BEST MODE OF THE INVENTION

Fluorine-Containing Silicone Polymer

The fluorine-containing silicone polymer of the present invention is a polymeric product having a three-dimensional, cross-linked structure obtained by addition polymerizing the following organopolysiloxane components, (A), (B) and (C), and is characterized by having the particular amounts, per molecule, of fluorine atoms and silicone side chains.

Components (A) and (B) may or may not comprise a siloxane unit represented by Rf in the aforementioned formulas (1) and (2). The present fluorine-containing silicone polymer comprises 10 to 30 mass %, preferably 15 mass % to 27 mass %, of fluorine atoms, relative to a total mass of components (A) to (C). If the fluorine content is lower than the aforementioned lower limit, the effects by the modification by fluorine-containing substituents are less, so that the light feeling and smoothness characteristic to the fluorine-containing compounds are less. If the fluorine content is higher than the aforementioned upper limit, their affinity with the low viscosity silicone oil (D) is lower and, therefore, the low viscosity silicone oil is less occluded in the three-dimensional, cross-linked structure formed by the addition polymerization and tends to separate.

The each component will be described below in detail.

(A) Vinyl Group-Containing Organopolysiloxane

Component (A) represented by the following formula (1) is an organopolysiloxane which has at least two, per molecule, vinyl groups bonded to silicon atoms.

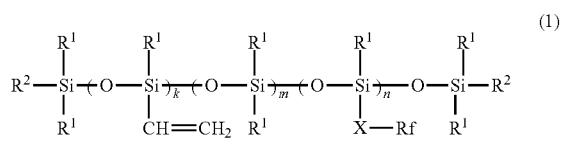

In the aforementioned formula (1), Rf is a perfluoroalkyl group having 1 to 10, preferably 3 to 6, carbon atoms or a perfluoropolyether group having 3 to 30, preferably 8 to 20, carbon atoms. Examples of the perfluoroalkyl groups include trifluoropropyl, nonafluorobutyl, tridecafluorohexyl, and heptadecafluorooctyl groups. Nonafluorobutyl and tridecafluorohexyl groups are preferred. Examples of the perfluoropolyether groups include those represented by the following formulas (4) and (5). In particular, the perfluoropolyether represented by formula (4) is preferred.

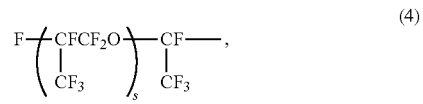

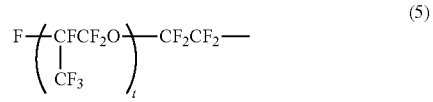

wherein s and t are each an integer of 1 to 9, preferably 2 to 5.

In the aforementioned formula (1), k is an integer of 0 to 10, m is an integer of 0 to 200, and n is an integer of 0 to 100. Preferably, k is an integer of 1 to 5, m is an integer of 50 to 120 and n is an integer of 5 to 30.

In the aforementioned formula (1), X is a divalent organic group, in particular, that having 2 to 12, preferably 2 to 8, carbon atoms and, optionally, may contain an oxygen and a nitrogen atom. Specific examples of X include the following.

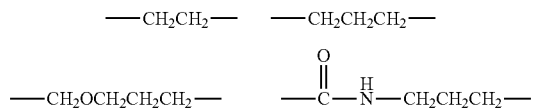

In the aforementioned formula (1), $R^1$ is, independently of each other, a monovalent hydrocarbon group having 1 to 10, preferably 1 to 4, carbon atoms without any aliphatic unsaturated bond. Examples of the monovalent hydrocarbon groups include lower alkyl groups, such as methyl, ethyl, propyl and butyl groups, cycloalkyl groups such as a cyclohexyl group, aryl groups such as phenyl, tolyl and xylyl groups and aralkyl groups such as a benzyl group. Methyl and n-butyl groups are preferred.

$R^2$ is, independently of each other, a vinyl group or a monovalent hydrocarbon group having 1 to 10, preferably 1 to 4, carbon atoms without any aliphatic unsaturated bond. Examples of the monovalent hydrocarbon groups include lower alkyl groups, such as methyl, ethyl, propyl and butyl groups, cycloalkyl groups such as a cyclohexyl group, aryl groups such as phenyl, tolyl and xylyl groups and aralkyl groups such as a benzyl group. $R^2$ is preferably a vinyl group. When k is 0, both of the $R^2$'s are a vinyl group. When k is 1, at least one of $R^2$'s is a vinyl group.

(B) Organohydrogenpolysiloxane

Component (B) is represented by the following formula (2) and has at least two hydrogen atoms, per molecule, bonded to silicon atoms so as to addition polymerize with component (A) to form a cross-linked structure.

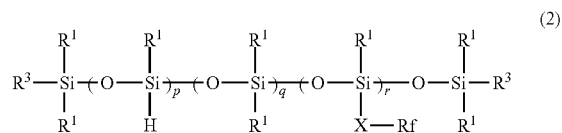

(2)

In the aforementioned formula (2), p is an integer of 0 to 10, q is an integer of 0 to 200 and r is an integer of 0 to 100. Preferably, p is an integer of 2 to 5, q is an integer of 1 to 50 and r is an integer of 0 to 20. It should be noted that n in the aforementioned formula (1) and r in the aforementioned formula (2) are not simultaneously zero. $R^3$ is, independently of each other, a hydrogen atom or a monovalent hydrocarbon group having 1 to 10, preferably 1 to 4, carbon atoms without any aliphatic unsaturated bond, and is preferably a methyl group. When p is 0, both of $R^3$'s are a hydrogen atom. When p is 1, at least one of $R^3$'s is a hydrogen atom. At least either one of the number of vinyl groups bonded to silicon atoms in formula (1) or the number of hydrogen atoms bonded to silicon atoms in formula (2) is at least three. $R^1$, X and Rf are as defined above.

(C) Organopolysiloxane Having a Reactive Group on One End Alone

Component (C) is an organopolysiloxane which bonds to component (A) and/or component (B) to form a silicone side chain. The silicone side chain in the fluorine-containing silicone polymer improves swellability of the silicone polymer with low viscosity silicone oils, and thus improves a thickening property and, consequently increases stability of the fluorine-containing organopolysiloxane composition. Component (C) of the present invention is represented by the following formula (3) and is an organopolysiloxane having a reactive group on one end alone, wherein the reactive group is either a hydrogen atom or a vinyl group bonded to a silicone atom.

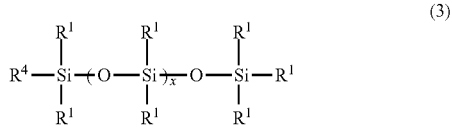

(3)

wherein $R^4$ is a hydrogen atom or a vinyl group. $R^1$ is, independently of each other, a monovalent hydrocarbon group having 1 to 10, preferably 1 to 4, carbon atoms without any aliphatic unsaturated bond. Examples of the monovalent hydrocarbon groups include lower alkyl groups, such as methyl, ethyl, propyl and butyl groups, cycloalkyl groups such as a cyclohexyl group, aryl groups such as phenyl, tolyl and xylyl groups and aralkyl groups such as a benzyl group. Methyl and n-butyl groups are preferred. X is an integer of 0 to 100, preferably 5 to 30.

The silicone side chain is introduced preferably into either component (A) or component (B) which has a higher fluorine content, whereby the silicone polymer is insoluble in the low viscosity silicone oil (D), but sufficiently swellable therewith to give the fluorine-containing organopolysiloxane composition which well occludes the low viscosity silicone oil (D) therein. When introducing the silicone side chain into component (A), component (C) where $R^4$ in the aforementioned formula (3) is a hydrogen atom is used in such an amount that the SiH group in component (C) is 0.1 to 0.4 mole, preferably 0.15 to 0.3 mole, per mole of the vinyl group in component (A). When introducing the silicone side chain into component (B), component (C) where $R^4$ in the aforementioned formula (3) is a vinyl group is used in such an amount that the vinyl group in component (C) is 0.1 to 0.4 mole, preferably 0.15 to 0.3 mole, per mole of the SiH group in component (B). If the amount of the reactive group in component (C) is lower than the aforementioned lower limit, the swellability of the silicone polymer with low viscosity silicone oils is bad and storage stability of the fluorine-containing organopolysiloxane composition is low. If the amount of the reactive group is higher than the aforementioned upper limit, only an insufficient amount of the reactive group remains in component (A) or (B) after introducing the silicone side chain and, accordingly, the three-dimensional, cross-linked structure is only poorly built up. Therefore, the low viscosity silicone oil is less occluded in the three-dimensional, cross-linked structure. Accordingly, when the low viscosity silicone oil (D) is used in a relatively large amount or when the fluorine-containing organopolysiloxane composition is used together with the low viscosity silicone oil (D) in processing the fluorine-containing organopolysiloxane composition by a shearing force, the fluorine-containing organopolysiloxane composition dissolves easily in the low viscosity silicone oil (D) and, therefore, the siloxane composition obtained cannot be sufficiently viscous, which is undesired.

Components (A) and (B) are reacted after the silicone side chain is introduced in (A) and/or (B), in such amounts that the SiH group in component (B) is 0.7 to 1.3 moles, preferably 0.8 to 1.1 moles, per mole of the vinyl group in component (A), whereby, the three-dimensional, cross-linked structure is formed as desired. Component (A) and component (B) preferably have the vinyl group or SiH group in the amount of 0.5 to 50 mole %. If the amount of the reactive group exceeds the aforementioned upper limit, density of the three-dimensional, cross-linked structure in the polymeric product is so high that it is difficult to occlude the low viscosity silicone oil (D) in the three-dimensional, cross-linked structure and, therefore, the low viscosity silicone oil bleeds out easily and the stability is low, which is undesired.

Fluorine-Containing Organopolysiloxane Composition

The addition polymerization of components (A), (B) and (C) may be carried out in the presence of the low viscosity silicone oil (D) described below. The present fluorine-containing organopolysiloxane composition comprises the silicone polymer obtained by addition polymerizing components (A), (B) and (C) and the low viscosity silicone oil (D). Another low viscosity silicone oil (D) different from the low viscosity silicone oil (D) present in the reaction may be added after the addition polymerization.

(D) Low Viscosity Silicone Oil

Component (D) is a low viscosity silicone oil having a dynamic viscosity at 25 degrees C. of 50 mm²/s or less, preferably 50 mm²/s to 0.65 mm²/s, more preferably 10 mm²/s to 0.65 mm²/s. If the dynamic viscosity exceeds 50 mm²/s, the silicone oil tends to bleeds out to make the composition unstable, and greasy touch appears and fresh feeling is lost, which is undesired. The low viscosity silicone oil is an organopolysiloxane having no functionality, that is, having no alkenyl group or SiH group which is bonded to a silicone atom and capable of participating in hydrosilylation. Examples of the low viscosity silicone oil include liner or branched methyl polysiloxane, methyl phenyl polysiloxane, ethyl polysiloxane, ethyl methyl polysiloxane and ethyl phenyl polysiloxane which all have a low polymerization degree, cyclic octamethylcyclotetrasiloxane and decamethylcyclopentasiloxane. One or more of these are properly selected, as required.

Component (D) is used suitably in an amount of 10 to 1000 parts by mass, preferably 20 to 700 parts by mass, more preferably 50 to 500 parts by mass, relative to 100 parts by mass of a total of components (A) to (C). If the amount of the low viscosity silicone oil is less than 10 parts by mass, the effects of the low viscosity silicone oil are so less that thickening property of the resulting composition is low; when the composition is blended with rubber or plastics, the effect of providing flexibility or a lubricating property is less, which is undesired; and further, the transparency of the composition obtained tends to be lost. If the amount of the low viscosity silicone oil (D) is larger than 1000 parts by mass, the reaction among components (A), (B) and (C) is less and, therefore, a composition does not have a sufficient thickening property. Preferably, 10 to 200 parts by mass, in particular 20 to 100 parts by mass, of component (D) is used in the addition reaction with 100 parts by mass of a total of components (A) to (C), whereby the reaction product gradually changes its form from a liquid, via a soft mass, to powder, as the polymerization proceeds.

The addition polymerization of components (A), (B) and (C) in the presence of the low viscosity silicone oil (D) may be carried out in any conventional method, for instance, at room temperature or under heating to approximately 50 to 150 degrees C. in the presence of an organic solvents-soluble platinum compound, such as chloroplatinic acid, alcohol-modified chloroplatinic acid or a complex of chloroplatinic acid with vinylsiloxane, or an organic rhodium compound. As the organic solvent, use may be made of aliphatic alcohols, such as methanol, ethanol, 2-propanol and butanol, aromatic hydrocarbons, such as benzene, toluene and xylene, aliphatic or alicyclic hydrocarbons, such as n-pentane, n-hexane and cyclohexane, and halogenated hydrocarbons, such as dichloromethane, chloroform, tetrachloromethane, trichloroethane, trichloroethylene and fluorinated and chlorinated hydrocarbons.

Examples of the catalyst preferably include chloroplatinic acid and platinum compounds, such as $Pt(PPh_3)_3$, which are used in hydrosilylation described in U.S. Pat. Nos. 3,159,601, 3,159,662 and 3,775,452. The platinum compounds are preferably complexes with, for instance, vinyl siloxane or those modified with alcohol. Inter alia, preferred is chloroplatinic acid or the complex of chloroplatinic acid with vinyl siloxane which are described in Japanese Patent Publication No. Sho-33-9969.

In an exemplary method for the addition polymerization, components (A), (B), (C) and (D) are blended in desired amounts in a reactor such as a planetary mixer equipped with a stirring equipment, and a catalyst is added, followed by stirring at an appropriate temperature, for instance, approximately 50 to 150 degrees C. Here, it is preferred that either component (A) or (B) which has a higher fluorine content is addition reacted with component (C) to introduce the silicone side chain into the organopolysiloxane chain of this (A) or (B) and, then, this organopolysiloxane is addition polymerized with the other organopolysiloxane. Such a two-step process does not lower the compatibility among components (A) to (C) and, therefore, the addition polymerization proceeds smoothly. If components (A) and (B) are addition polymerized first, the reactivity for forming the silicone side chains is very low. If components (A) to (C) are fed at once and reacted simultaneously, cross-links are formed before a desired amount of the silicone side chains is introduced into the main chain, i.e., organopolysiloxane backbone, and, therefore, the amount of the side chains is less, whereby the characteristics of the silicone side chains is not sufficiently exerted.

The present composition changes its form from a liquid, via a soft mass, to powder as the polymerization proceeds. In order to obtain a composition in a state of fine powder, the composition obtained in a state of powder is processed by a shearing force. The powder composition is pulverized in this processing to give fine powder of the composition. This fine powder composition does not show bleed-out on the surface, is white, homogeneous in composition, smooth in touch and flexible to a proper extent.

In order to obtain a pasty composition or a greasy composition, the low viscosity silicone oil (D) may be further added to the lump or powder composition, which is then processed by a shearing force. The low viscosity silicone oil is added in such an amount that a total amount of the low viscosity silicone oil contained in the fluorine-containing organopolysiloxane composition is 10 to 1000 parts by mass, preferably 20 to 700 parts by mass, more preferably 50 to 500 parts by mass, relative to 100 parts by mass of a total of components (A) to (C). The aforementioned processing gives a kneaded and homogeneous fluorine-containing organopolysiloxane composition. If the amount of the low viscosity silicone oil is less than 10 parts by mass, the resulting composition is not in a homogeneous, pasty form. If the amount of the low viscosity silicone oil exceeds 1000 parts by mass, the end product does not acquire a sufficient thickening property and, therefore, is not in a good pasty or greasy state.

A relatively highly viscous, homogeneous and pasty composition with smooth appearance is obtained by processing the polymerization composition by a shearing force as mentioned above. If the shearing force is not applied or insufficient, the fluorine-containing silicone polymer dissolves insufficiently in the low viscosity silicone oil, so that the fluorine-containing silicone polymer and the low viscosity silicone oil do not mix with each other and provide an unhomogeneous composition, whereby the composition is low viscous and does not have a sufficient thickening property. Further, a less-swelled fluorine-containing silicone polymer remains in the end composition whose touch is, therefore, rough and the appearance is coarse. The processing by a shearing force can be carried out by a kneading means, such as a three-roll mill, a two-roll mill, a sand grinder, a colloid mill and a Gaulin homogenizer. The kneading means may be selected properly, depending on the properties and state of the material to be processed. Inter alia, processing by a three-roll mill is preferred.

EXAMPLES

The present invention will be described in detail by referring to the Examples and the Comparative Examples below, but is not limited thereto.

Example 1

To a planetary mixer were added 100.0 g of the vinyl group-containing organopolysiloxane represented by the following formula (6) (fluorine content: 25.5% by mass; vinyl group content: $2.96 \times 10^{-2}$ mol/100 g):

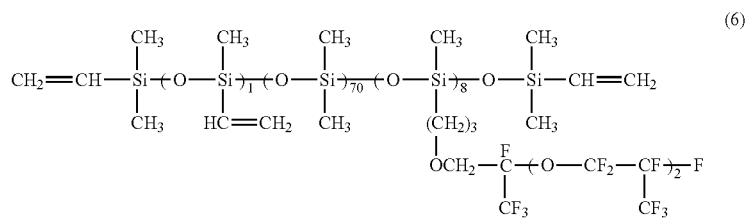

(6)

5.27 g of the organohydrogenpolysiloxane represented by the following formula (7)(SiH group content: $5.64 \times 10^{-3}$ mol/5.27 g):

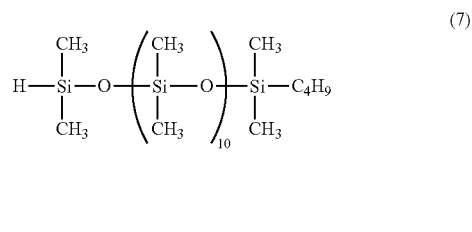

(7)

and 165.8 g of dimethylpolysiloxane having a dynamic viscosity of 2 mm²/s. 0.017 Gram of a solution of a complex of platinum with vinyl siloxane in toluene (corresponding to 0.17 mg of Pt) was added and stirred at 80 degrees C. for 1 hour.

Then, to the aforementioned reaction mixture were added 5.26 g of the organohydrogenpolysiloxane represented by the following formula (8) (fluorine content: 18.4% by mass; SiH content: $2.26 \times 10^{-2}$ mol/5.26 g):

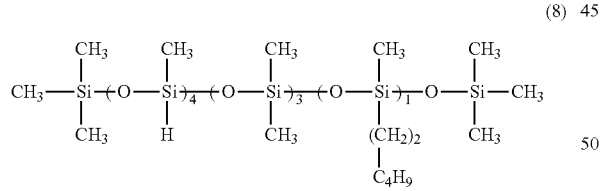

(8)

and 0.017 g of the aforementioned solution of the platinum complex and stirred at 80 degrees C. for another 1 hour to obtain a dispersion of a silicone polymer in dimethylpolysiloxane. The dispersion of the silicone polymer obtained was white and flexible powder with a fluorine content in the silicone polymer of 23.9% by mass, calculated precluding the dimethylpolysiloxane (hereinafter referred to as "silicone polymer 1").

100.0 Parts by mass of the aforementioned silicone polymer 1 and 150.0 parts by mass of dimethylpolysiloxane with a dynamic viscosity of 2 mm²/s were mixed to disperse and kneaded by a shearing force by a three-roll mill, so that the silicone polymer swelled with the dimethylpolysiloxane to give a colorless and transparent pasty organopolysiloxane composition.

Example 2

To a planetary mixer were added 100.0 g of the vinyl group-containing organopolysiloxane represented by the following formula (9) (fluorine content: 20.6% by mass; vinyl group content: $3.61 \times 10^{-2}$ mol/100 g):

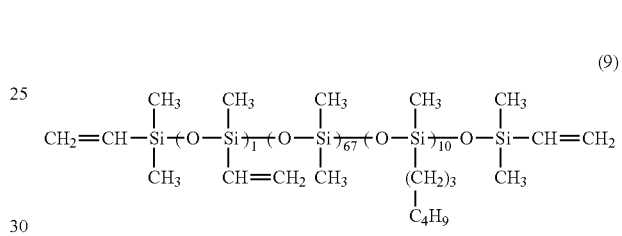

(9)

6.43 g of the organohydrogenpolysiloxane represented by the aforementioned formula (7) (SiH group content: $6.88 \times 10^{-3}$ mol/6.43 g), and 110.3 g of decamethylpentasiloxane having a dynamic viscosity of 4 mm²/s. 0.017 Gram of a solution of a complex of platinum with vinyl siloxane in toluene (corresponding to 0.17 mg of Pt) was added and stirred at 80 degrees C. for 1 hour.

Then, to the aforementioned reaction mixture were added 3.83 g of the organohydrogenpolysiloxane represented by the following formula (10) (SiH group content: $2.75 \times 10^{-2}$ mol/3.83 g):

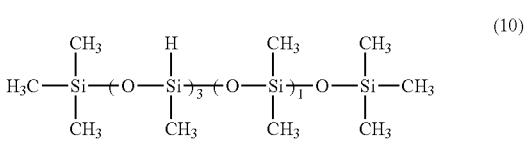

(10)

and 0.017 gram of the solution of the complex of platinum with vinyl siloxane in toluene and stirred at 80 degrees C. for another 1 hour to obtain a silicone polymer dispersion in decamethylcyclopentasiloxane. The obtained dispersion of the silicone polymer was white and flexible powder with a fluorine content in the silicone polymer of 18.7% by mass, calculated precluding the decamethylcyclopentasiloxane (hereinafter referred to as "silicone polymer 2").

100.0 Parts by mass of the aforementioned silicone polymer 2 and 200.0 parts by mass of decamethylcyclopentasiloxane were mixed to disperse and kneaded by a shearing force by a three-roll mill, so that the silicone polymer swelled with the decamethylcyclopentasiloxane to give a colorless and transparent pasty organopolysiloxane composition.

Example 3

To a planetary mixer were added 100.0 g of the organohydrogenpolysiloxane represented by the following formula (11) (fluorine content: 24.9% by mass; SiH group content: $6.03 \times 10^{-2}$ mol/100 g):

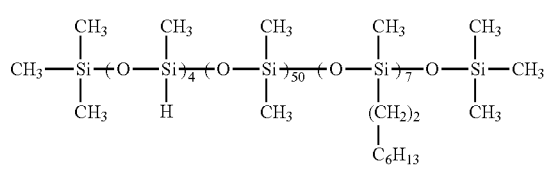
(11)

8.90 g of the organopolysiloxane represented by the following formula (12) (vinyl group content: $1.09 \times 10^{-2}$ mol/8.90 g):

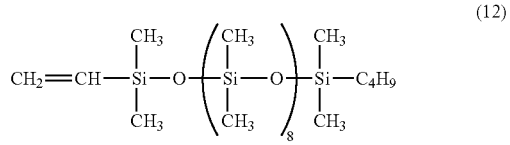
(12)

and 188.4 g of tristrimethylsiloxymethylsilane with a dynamic viscosity of 1.5 mm²/s. 0.028 Gram of a solution of a complex of platinum with vinyl siloxane in toluene (corresponding to 0.28 mg of Pt) was added and stirred at 80 degrees C. for 1 hour.

Then, to the aforementioned reaction mixture were added 79.5 g of the vinyl group-containing organopolysiloxane represented by the following formula (13) (fluorine content: 20.4% by mass; vinyl group content: $4.38 \times 10^{-2}$ mol/79.5 g):

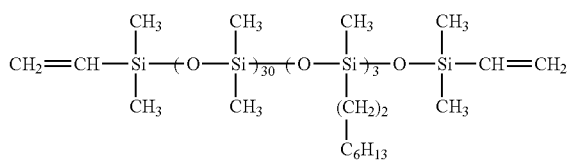
(13)

and 0.028 g of the aforementioned solution of the complex of platinum and stirred at 80 degrees C. for another 1 hour to obtain a dispersion of the silicone polymer in tristrimethylsiloxymethylsilane. The obtained dispersion of the silicone polymer was white and flexible powder with a fluorine content in the silicone polymer of 21.8% by mass, calculated precluding the tristrimethylsiloxymethylsilane (hereinafter referred to as "silicone polymer 3").

100.0 Parts by mass of the aforementioned silicone polymer 3 and 250.0 parts by mass of tristrimethylsiloxymethylsilane were mixed to disperse and kneaded by a shearing force by a three-roll mill, so that the silicone polymer swelled with the tristrimethylsiloxymethylsilane to give a colorless and transparent pasty organopolysiloxane composition.

Example 4

To a planetary mixer were added 100.0 g of the vinyl group-containing organopolysiloxane represented by the following formula (14) (fluorine content: 25.9% by mass; vinyl group content: $3.25 \times 10^{-2}$ mol/100 g):

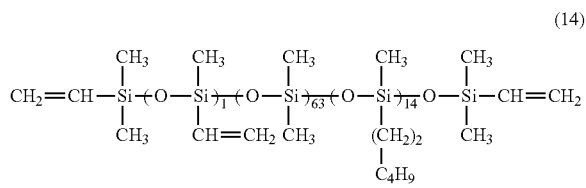
(14)

6.57 g of the organohydrogenpolysiloxane represented by the aforementioned formula (7) (SiH group content: $6.88 \times 10^{-3}$ mol/6.57 g) and 109.9 g of dimethylpolysiloxane with a dynamic viscosity of 2 mm²/s. 0.017 Gram of a solution of a complex of platinum with vinyl siloxane in toluene (corresponding to 0.17 mg of Pt) was added and stirred at 80 degrees C. for 1 hour.

Then, to the aforementioned reaction mixture was added 3.36 g of the organohydrogenpolysiloxane represented by the aforementioned formula (10) (SiH group content: $2.42 \times 10^{-2}$ mol/3.36 g) and 0.017 g of the aforementioned solution of the complex of platinum were added and stirred at 80 degrees C. for another 1 hour to obtain a dispersion of the silicone polymer in dimethylpolysiloxane. The obtained dispersion of the silicone polymer was white and flexible powder with a fluorine content in the silicone polymer of 23.6% by mass, calculated precluding the dimethylpolysiloxane (hereinafter referred to as "silicone polymer 4").

100.0 Parts by mass of the aforementioned silicone polymer 4 and 185.7 parts by mass of dimethylpolysiloxane with a dynamic viscosity of 2 mm²/s were mixed to disperse and kneaded by a shearing force by a three-roll mill, so that the silicone polymer swelled with the dimethylpolysiloxane to give a colorless and transparent pasty organopolysiloxane composition.

Comparative Example 1

To a planetary mixer were added 100.0 g of the vinyl group-containing organopolysiloxane represented by the following formula (15) (fluorine content: 20.6% by mass, vinyl group content: $2.41 \times 10^{-2}$ mol/100.0 g):

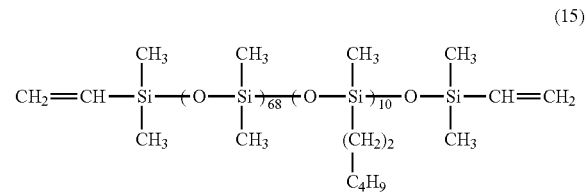
(15)

3.19 g of the organohydrogenpolysiloxane represented by the aforementioned formula (10) (SiH group content: $2.29 \times 10^{-2}$ mol/3.19 g), and 113.2 g of decamethylcyclopentasiloxane having a dynamic viscosity of 4 mm²/s. 0.034 Gram of a solution of a complex of platinum with vinyl siloxane in toluene (corresponding to 0.34 mg of Pt) was added and stirred at 80 degrees C. for another 1 hour to obtain a dispersion of the silicone polymer in decamethylcyclopentasiloxane. The obtained dispersion of the silicone polymer was white and flexible powder with a fluorine content in the silicone polymer of 20.0% by mass, calculated precluding the decamethylcyclopentasiloxane (hereinafter referred to as "silicone polymer 5").

100.0 Parts by mass of the aforementioned silicone polymer 5 and 200.0 parts by mass of decamethylcyclopentasiloxane were mixed to disperse and kneaded by a shearing force by a three-roll mill, so that the silicone polymer swelled with the decamethylcyclopentasiloxane to give a colorless and transparent pasty organopolysiloxane composition.

Comparative Example 2

To a planetary mixer were added 100.0 g of the vinyl group-containing organopolysiloxane represented by the following formula (16) (fluorine content: 35.4% by mass, vinyl group content: $2.19 \times 10^{-2}$ mol/100.0 g):

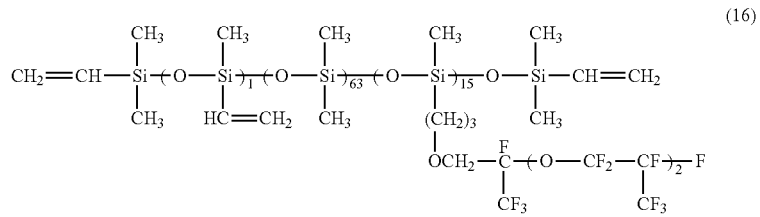

(16)

3.90 g of the organohydrogenpolysiloxane represented by the aforementioned formula (7) (SiH group content: $4.17 \times 10^{-3}$ mol/3.90 g), and 159.3 g of dimethylpolysiloxane having a dynamic viscosity of 2 mm$^2$/s. 0.016 Gram of a solution of a complex of platinum with vinyl siloxane in toluene (corresponding to 0.16 mg of Pt) was added and stirred at 80 degrees C. for 1 hour. Then, 2.32 g of the organohydrogenpolysiloxane represented by the aforementioned formula (10) (SiH group content: $1.67 \times 10^{-2}$ mol/2.32 g) and 0.016 g of the aforementioned solution of the complex of platinum were added and stirred at 80 degrees C. for another 1 hour to obtain a dispersion of the silicone polymer in dimethylpolysiloxane. The obtained dispersion of the silicone polymer was white and flexible powder with a fluorine content in the silicone polymer of 33.3% by mass, calculated precluding the dimethylpolysiloxane (hereinafter referred to as "silicone polymer 6").

100.0 Parts by mass of the aforementioned silicone polymer 6 and 150.0 parts by mass of dimethylpolysiloxane having a dynamic viscosity of 2 mm$^2$/s were mixed to disperse and kneaded by a shearing force by a three-roll mill, so that the silicone polymer swelled with the dimethylpolysiloxane to give a colorless and transparent pasty organopolysiloxane composition.

Comparative Example 3

A silicone composition which was obtained by kneading a dimethylpolysiloxane polymer with decamethylcyclopentasiloxane to swell (trade name: KSG-15, ex Shin-Etsu Chemical Co., Ltd.)

Comparative Example 4

To a planetary mixer were added 100.0 g of the vinyl group-containing organopolysiloxane represented by the aforementioned formula (16) (fluorine content: 35.4% by mass, vinyl group content: $2.19 \times 10^{-2}$ mol/100 g), 3.05 g of the organohydrogenpolysiloxane represented by the aforementioned formula (10) (SiH group content: $2.19 \times 10^{-2}$ mol/3.05 g), and 102.9 g of dimethylpolysiloxane having a dynamic viscosity of 2 mm$^2$/s. 0.012 Gram of a solution of a complex of platinum (corresponding to 0.12 mg of Pt) was added and stirred at 80 degrees C. for another 1 hour to obtain a dispersion of the silicone polymer in dimethylpolysiloxane. The obtained dispersion of the silicone polymer was white and flexible powder with a fluorine content in the silicone polymer of 34.4% by mass, calculated precluding the dimethylpolysiloxane (hereinafter referred to as "silicone polymer 7").

100.0 Parts by mass of silicone polymer 7 and 150.0 parts by mass of dimethylpolysiloxane having a dynamic viscosity of 2 mm$^2$/s were mixed to disperse and kneaded by a shearing force by a three-roll mill, but the silicone polymer did not swell and remained in such a state that powder was dispersed in dimethylpolysiloxane. Accordingly, this composition was not subjected to the following evaluation.

Examples 1 to 4 and Comparative Example 1 to 3

The organopolysiloxane compositions of Examples 1 to 4 and Comparative Examples 1 to 3 were evaluated on the following properties. The results are as shown in Table 1.

[Water- and Oil-Repellency]

0.20 Gram of the organopolysiloxane composition was applied uniformly on a glass slide of 26 mm by 76 mm and dried at 150 degrees C. for 1 hour. Then, the glass slide was cooled to room temperature and a contact angle to water was measured by a contact angle meter to evaluate water repellency. Oil repellency was evaluated by measuring a contact angle to n-hexadecane instead of water in the same manner.

[Dispersibility]

20.0 Grams of the organopolysiloxane composition and 80.0 g of decamethylcyclopentasiloxane were placed in a 200 cc flask and dispersed by a homodisper, ex Primix Corporation, for 15 minutes. The flask was left to stand still for 30 minutes and the state of dispersion was observed with the naked eye to evaluate the dispersibility.

[Affinity]

20.0 Grams of the organopolysiloxane composition and 80.0 g of isododecane were placed in a 200 cc flask and dispersed by a homodisper of a type 2.5, ex Primix Corporation, for 15 minutes. The flask was left to stand still for 30 minutes and the state of dispersion was observed with the naked eye to evaluate the affinity with organic solvents.

[Storage Stability]

The organopolysiloxane composition was placed in a sealed container and stored at 40 degrees C. for one week. The appearance of the composition was observed with the naked eye to evaluate the storage stability.

[Touch]

To evaluate light feeling and greasy touch, 20 panelists were applied with the organopolysiloxane composition on the backs of their hands and evaluated the touch of the composition.

TABLE 1

| Evaluation item | Water reppelency, deg | Oil repellency, deg | Dispersibility | Affinity | Storage stability | Touch Light feeling | Touch Greasy touch |
|---|---|---|---|---|---|---|---|
| Example 1 | 102 | 40 | Good | Good | Good | Light | None |
| Example 2 | 100 | 36 | Good | Good | Good | Very light | None |
| Example 3 | 104 | 38 | Good | Good | Good | Light | None |
| Example 4 | 101 | 37 | Good | Good | Good | Very light | None |
| Comparative Example 1 | 100 | 36 | Good | Good | Creep hardening | Slightly heavy | Slightly remained |
| Comparative Example 2 | 106 | 41 | Settled | Settled | Oil separated | Light | Remained |
| Comparative Example 3 | 88 | <20 | Good | Good | Good | Heavy | Remained |

As seen in Table 1, the composition of Comparative Example 1, which comprises the fluorine-containing silicone polymer having no silicone side chain, has bad swellability with low viscosity silicone oil and, accordingly, the bad storage stability. The composition of Comparative Example 2, which comprises the polymer with the too high fluorine content, has the bad affinity with low viscosity silicone oil and, therefore, the dispersibility is bad and the oil separates. The compatibility with organic solvent is also bad. The composition of Comparative Example 3, which comprises a polymer having no fluorine atom, is bad in water-repellency. Meanwhile, the pasty compositions comprising the present silicone polymer are good in storage stability, and pasty and homogeneous, and provides very light feeling and smooth touch. The affinity with organic solvent is also good.

Industrial Applicability

The present fluorine-containing organopolysiloxane composition provides a homogenous pasty composition which is good in water- and oil-repellency, swellable with low viscosity silicone oils, and good in storage stability and, therefore, is suitably used, in particular, as a base material in cosmetic. The present fluorine-containing organopolysiloxane composition is good in affinity with other materials and, therefore, useful as additives in cosmetics, cleaners and waxes in the field of household products, as mold release agents for improving a releasing property in molding, additives for providing grease with water- and oil-repellency, additives for improving an anti-abrasion property of lubricants, adjuvants for improving a coloring property and dispersibility of pigments in the field of dye and pigment industries, and agents for providing a leveling property or anti-cratering property for compensating defects in coating.

The invention claimed is:

1. A fluorine-containing organopolysiloxane composition comprising a fluorine-containing silicone polymer having a three-dimensional, cross-linked structure, prepared by addition polymerizing the following (A), (B) and (C) and containing 10 to 30 mass % of the fluorine atoms, relative to a total mass of (A) to (C), (A) a vinyl group-containing organopolysiloxane represented by the following formula (1):

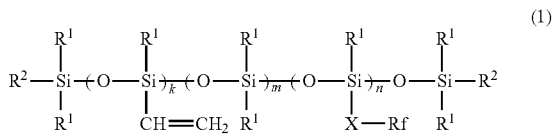

wherein Rf is a perfluoroalkyl group having 1 to 10 carbon atoms or a perfluoropolyether group having 3 to 30 carbon atoms; $R^1$ is, independently of each other, a monovalent hydrocarbon group having 1 to 10 carbon atoms without any aliphatic unsaturated bond; $R^2$ is, independently of each other, a vinyl group or a monovalent hydrocarbon group having 1 to 10 carbon atoms without any aliphatic unsaturated bond; k is an integer of 0 to 10, provided that the organopolysiloxane has at least two, per molecule, vinyl groups bonded to silicon atoms; X is a divalent organic group, m is an integer of 0 to 200, and n is an integer of 0 to 100, (B) an organohydrogenpolysiloxane represented by the following formula (2):

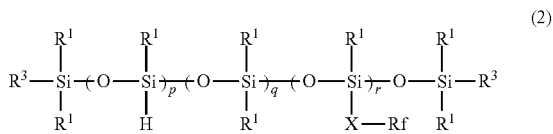

wherein $R^3$ is, independently of each other, a hydrogen atom or a monovalent hydrocarbon group having 1 to 10 carbon atoms without any aliphatic unsaturated bond; p is an integer of 0 to 10, provided that the organopolysiloxane has at least two, per molecule, hydrogen atoms bonded to silicon atoms; q is an integer of 0 to 200; r is an integer of 0 to 100, provided that n in formula (1) and r in formula (2) are not simultaneously zero; and at least either one of the number of the vinyl groups bonded to silicon atoms in formula (1) or the number of the hydrogen atoms bonded to silicon atoms in formula (2) is at least three; and Rf, X, and $R^1$ are as defined above, and (C) an organopolysiloxane having a reactive group on one end alone and represented by the following formula (3),

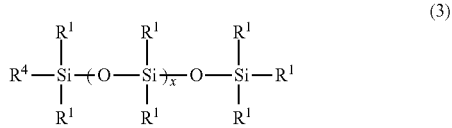

wherein $R^4$ is a hydrogen atom or a vinyl group, x is an integer of 0 to 100, and $R^1$ is as defined above, and further comprising (D) a low viscosity silicone oil with a dynamic viscosity of 50 mm²/s or less at 25 degrees C., wherein the content of the low viscosity silicone oil (D) is 10 to 1000 parts by mass relative to 100 parts by mass of a total of components (A) to (C).

2. The fluorine-containing organopolysiloxane composition according to claim 1, wherein the composition is in a state of fine powder, paste or grease.

3. A process for preparing the fluorine-containing organopolysiloxane composition described in claim 2, comprising a step of addition polymerizing components (A), (B) and (C) in the presence of the low viscosity silicone oil (D).

4. A process for preparing the fluorine-containing organopolysiloxane composition described in claim 1, comprising a step of addition polymerizing components (A), (B) and (C) in the presence of the low viscosity silicone oil (D).

5. The process for preparing the fluorine-containing organopolysiloxane composition according to claim 4, further comprising a step of adding the low viscosity silicone oil (D) after the addition polymerizing components (A), (B) and (C) in the presence of the low viscosity silicone oil (D).

6. The process for preparing the fluorine-containing organopolysiloxane composition according to claim 5, further comprising a step of processing the polymerization mixture by a shearing force after adding the low viscosity silicone oil (D).

7. The process for preparing the fluorine-containing organopolysiloxane composition according to claim 4, further comprising a step of processing the polymerization mixture by a shearing force after addition polymerizing the step.

* * * * *